United States Patent

Pribat et al.

Patent Number: 5,429,737
Date of Patent: Jul. 4, 1995

[54] ELECTROCHEMICAL SENSOR WITH INTEGRATED STRUCTURE FOR THE MEASUREMENT OF RELATIVE CONCENTRATIONS OF REACTIVE SPECIES

[75] Inventors: Didier Pribat, Paris; Joël Perret, Plaisir; Jean C. Rouffy, Poissy; Gonzalo Velasco, Paris, all of France

[73] Assignee: Thomson-CSF, Paris, France

[21] Appl. No.: 103,314

[22] Filed: Aug. 9, 1993

Related U.S. Application Data

[63] Continuation of Ser. No. 888,274, May 26, 1992, abandoned, which is a continuation of Ser. No. 722,389, Jun. 26, 1991, abandoned, which is a continuation of Ser. No. 569,389, Aug. 15, 1990, abandoned, which is a continuation of Ser. No. 247,646, Sep. 22, 1988, abandoned.

[30] Foreign Application Priority Data

Sep. 25, 1987 [FR] France ............... 87 13290

[51] Int. Cl.⁶ .......................... G01N 27/409
[52] U.S. Cl. .................... 204/426; 204/424; 204/429; 427/125; 427/126.2; 427/126.3
[58] Field of Search ............ 204/153.18, 421-429

[56] References Cited

U.S. PATENT DOCUMENTS

| | | | |
|---|---|---|---|
| 3,785,947 | 1/1974 | Baldwin et al. | 204/422 |
| 4,061,117 | 12/1977 | Ikeura | 204/428 |
| 4,272,350 | 6/1981 | Croset et al. | 204/426 |
| 4,277,323 | 7/1981 | Muller et al. | 204/425 |
| 4,283,261 | 8/1981 | Maurer et al. | 204/428 |
| 4,334,974 | 6/1982 | Muller et al. | 204/426 |
| 4,502,939 | 3/1985 | Holfelder et al. | 204/426 |
| 4,505,807 | 3/1985 | Yamada | 204/426 |
| 4,588,494 | 5/1986 | Kato et al. | 204/426 |
| 4,741,817 | 5/1988 | Croset et al. | 204/426 |
| 4,750,256 | 6/1988 | Wertheimer et al. | 204/424 |

FOREIGN PATENT DOCUMENTS

| | | |
|---|---|---|
| 0052542 | 5/1982 | European Pat. Off. . |
| 2449887 | 9/1980 | France . |

OTHER PUBLICATIONS

Patent Abstracts of Japan, vol. 9, No. 177 (p.–375) [1900], Jul. 23, 1985.
Patent Abstracts of Japan, vol. 10, No. 15 (p–422) [2072] Jan. 21, 1986.

*Primary Examiner*—T. Tung
*Attorney, Agent, or Firm*—Oblon, Spivak, McClelland, Maier & Neustadt

[57] ABSTRACT

In an electrochemical sensor, a gas analyzing electrochemical cell is implanted directly on a substrate wafer. The entire wafer is coated with enamel layers except at the places needed for the electrical connections. A fixing part fixes the sensor in a housing in such a way that the electrochemical cell is inside the housing which contains the gas to be analyzed. This fixing part provides imperviousness and prevents the gases from reaching the electrical connections.

7 Claims, 10 Drawing Sheets

ELECTROCHEMICAL SENSOR WITH INTEGRATED STRUCTURE FOR THE MEASUREMENT OF RELATIVE CONCENTRATIONS OF REACTIVE SPECIES

This application is a continuation-in-part of application Ser. No. 07/888,274, filed on May 26, 1992, now abandoned, which is a continuation of Ser. No. 07/722,389, filed on Jun. 26, 1991, now abandoned, which is a continuation of Ser. No. 07/569,389, filed Aug. 15, 1990, now abandoned, which is a continuation of Ser. No. 07/247,646, filed Sep. 22, 1988, now abandoned.

BACKGROUND OF THE INVENTION

1. Field of the Invention

The invention concerns an electrochemical sensor with an integrated structure for the measurement of concentrations of reactive species and, more particularly, to a sensor made with thin layer or thick layer type technologies on a substrate that is electrically insulating and chemically inert at high temperature.

The invention can also be applied, in particular, to the making of an oxygen concentration sensor which can be used, inter alia, in the automobile industry.

2. Description of the Prior Art

One of the well-known groups of electrochemical sensors works on the principle of the concentration cell and measures the partial pressure of one or more species of the gaseous mixture to be analyzed. This gaseous mixture, which is present in a first compartment and is, for example, an inert gas/oxygen mixture, is separated from a reference medium by the wall of a solid electrolyte, each face of which has an electrode. As is well known, the equations that govern the working of these sensors are: at the electrodes/electrolyte interfaces:

$$O_2 \underset{+4e^-}{\overset{-4e^-}{\rightleftarrows}} 2O^{2-} \quad (1)$$

the voltage $V_{E1/E2}$ which then develops between the electrodes is given by Nernst's law:

$$V_{E1/E2} = \frac{RT}{4F} \ln \frac{P_1}{P_2} \quad (2)$$

with

R = perfect gases constant = 8.314 J.(mole.K)$^{-1}$
F = Faraday No. = 96490 Coulombs
T = absolute temperature in degrees Kelvin
$P_1$ and $P_2$ = partial pressures of media 1 and 2 in the compartments 1 and 2.

Thus, knowledge of the temperature and of one of the partial pressures enables the unambiguous determining of the other partial pressure.

Should the mixture be reactive, for example, if it is a mixture of $O_2 + CO$, and if the electrode is a catalyst of the reaction of these gases, the following reaction occurs:

$$2CO + O_2 \rightleftarrows 2CO_2 \quad (3)$$

and, finally, if the combustion is complete until reversible thermodynamic equilibrium is achieved, the following relationship is verified:

$$\frac{[P\,CO][P\,O_2]^{\frac{1}{2}}}{[P\,CO_2]} = K(T) \quad (4)$$

with K(T) being a coefficient of equilibrium dependent on the temperature, and P CO, P $O_2$, P $CO_2$, being the partial pressures of carbon dioxide, oxygen and carbonic gas.

In applications concerning the regulation of automobile engines with spark ignition, in order to determine the partial pressure of oxygen at the exhaust (medium 1 for example), knowing the reference pressure (medium 2 which is generally air) in removing the need to measure or regulate the temperature, use is made of the fact that, if the exhaust gases are brought to thermodynamic equilibrium (end of combustion), the value of the partial pressure of oxygen, as shown in FIG. 1, varies by about 15 orders of magnitude when the mixture feeding the cylinders passes through the stoichiometric state.

Thus, in the above-described Nernst formula, a voltage leap is observed when the mixture passes the stoichiometric state $\Delta V = (RT/4F) \log PO_2^{rich}/PO_2^{poor}$; if the temperature is in the range of 800° C., the term RT/4F is of the order of 50 mV and the $\Delta V$ will be greater than 750 mV.

Sensors of this type, called stoichiometrical sensors, generally consist of a glove finger made of stabilized zircon. The external wall, provided with a porous platinum electrode (measuring electrode), is in contact with the gas for which it is sought to analyze the oxygen content and the inner wall, also provided with a platinum electrode (reference electrode), is in contact with a reference gas, generally air. The platinum of the measuring electrode catalyzes the end of combustion of the exhaust gases for example and, in order not to saturate the platinum, it is encapsulated by means of a porous diffusion layer, the main effect of which is to limit the flow of gases reaching the catalytic sites of the platinum electrode.

FIG. 2 shows a few typical responses of these glove finger sensors using air as a reference.

However, the making of sensors of this type may take different forms. FIGS. 3 and 4 show examples of embodiments obtained from successive deposits (thin layers or thick layers) of ceramic and metallic materials on an electrically insulating substrate. According to FIG. 3, there is a known method to make an electrochemical sensor comprising a solid electrolyte EL on a substrate Sb. This electrolyte may be made of zirconium oxide, thoria or cerium oxide stabilized by one or more elements belonging to columns $II_A$ and $III_B$ of the periodic classification of elements. It may be made as a thin layer or a thick layer, or it may be massive.

Electrodes E1/P1 and E2/P2 are deposited on the electrolyte EL and on the substrate Sb. The electrodes E1/P1 and E2/P2 are located in one and the same plane. The electrode E1/P1 combines the functions of an electrode and a reference medium. The electrode E1/P1 is further protected from the external environment by an impervious and inert insulating material S1 which coats it. It is possible, for example, to use an association of the type Ni/NiO or Pd/PdO to make this electrode/reference medium. The electrode E2/P2 has two zones and communicates directly with the medium to be analyzed in which there flows the gaseous mixture G through a hole made in the insulating body S1 which also covers it. In the first zone Ct, the electrode is not in contact with the electrolyte EL. The fluid to be analyzed must flow through the zone Ct which takes the place of a catalyst and a test sample inlet chamber. In this zone, the reactive species of the mixture to be analyzed (for example, in the case of exhaust gases: CO and $O_2$) are brought to complete thermodynamic equilibrium before they have reached the electrochemical cell itself:

E2/P2—EL—E1/P1

P2 represents the partial pressure of oxygen after catalysis in the real medium to be analyzed. The catalysis, which enables obtaining thermodynamic equilibrium, is achieved by the fact that the fluid flows through the catalyst in a direction parallel to the plane of the electrodes. The electrodes are extended outwards by metallic links to which the contacts C1 and C2 may be soldered. These links are made with platinum veneer for example. In one practical embodiment, the metallic links and the electrodes are made so as to form a single part. The substrate Sb may consist of a material (such as corundum) which insulates well at the operating temperature of the device and gives the unit mechanical strength. The face of the substrate 1 opposite the electrochemical cell has a heating resistor RC which enables accelerating the reaction.

The deposits can be made by well known techniques, such as: vacuum deposition (cathode spraying, evaporation), vapor phase deposition, electrochemical deposition or ion implantation or by a combination of two or more of these techniques. For a metal/oxidated metal reference mixture, such as Pd/PdO, the response, in voltage, to a temperature of about 800° C. is shown in FIG. 2 for the corresponding temperature (at 800° C., the pressure of equilibrium of the Pd/Po mixture is equal to 0.2 Atm.).

The descriptions of sensors thus made will be found in the French patents Nos. 2441 164 and 2 444 272.

FIG. 5 shows another embodiment of a sensor according to the prior art.

This figure repeats the elements illustrated with reference to FIG. 3: the measuring cell E1/P1-El1-E2/P2, deposited in thin or thick layers or in massive form on a substrate Sb, the catalysis region Ct and the test samples inlet region $P_{es}$ where the interactions with the gaseous mixture to be analyzed take place. In fact, in the example described, these latter two regions consist of an extension of the measuring electrode E2/P2. The output signal VS of the sensor is transmitted to external circuits (not shown) by connections C1 and C2. The two electrodes E1/P1 and E2/P2 should at least be shielded by an impervious and inert insulating jacket S1, made of enamel for example.

According to the sensor of FIG. 5, an additional electrochemical cell is integrated into the sensor and comprises a solid electrolyte El2 inserted between two electrodes E3 and E4. In the exemplary embodiment of FIG. 5, and according to the first approach, the second electrode E4 is identified with the extension of the measuring electrode E2. The cell is flush with the surface of the insulating material S1 so as to communicate with a medium containing oxygen. This medium may be the medium Mex in which there flows the gaseous mixture G to be analyzed. The cell E3-El2-E4 is supplied with a control current Ip by means of the connections C3 and C4, C4 being identified wth C2. The substrate face opposite to the electrocemical cell also has a heating resistor RC.

Referring again to the above description, it is immediately seen that the cell E3-El2-E4, working as an ion pump, modifies the oxygen composition of the test sample let into into the sensor, namely the oxygen composition of the gaseous mixture flowing towards and through the catalysis zone Ct to subsequently reach the measuring cell E2/P2-El1-E1/P1, and does this modification as a function of the amplitude and bias of the current Ip. It follows therefrom that this cell produces an output signal VS which flips over, no longer when the stoichiometric state of the mixture G is reached but "before" or "after" said stoichiometric state, the lag on either side of the stoichiometric state being defined continuously by the amplitude and bias of the control current Ip. FIG. 6 shows some typical responses of this type of sensor as a function of the bias current Ip.

A description of a sensor of this type will be found in the French patent No. 2 494 445 and 2 442 444.

In the present state of the art, the sensors, which have rectangular dimensions of 8 mm×2 mm, are manufactured collectively on square (3 inch×3 inch) or circular ($\emptyset$=3 inches) corundum substrates which are then cut out with a diamond saw or by laser ($CO_2$ or YAG). Each sensor is then mounted and wired to a flat support (strip) of alumina or any other electrical insulating material which enables the conveying of the various electrical input and output signals, through electrically conducting tracks, between the medium to be analyzed and the electronic control elements for the composition of the fluid mixture or the measurement of the oxygen rate. This strip supporting the sensor is itself then mounted in a cylindrical insulating element made of ceramic which enables it to be matched to the inside of a metallic part similar to an automobile spark plug body. The connections between the sensor and the external medium are made by means of electrical conducting tracks deposited on the supporting strip and connected to the other end of the strip to a connector. For example, when checking the air/gasoline mixture feeding the automobile engines, the medium analyzed consists of gas flowing in the exhaust silencer, and the data given by the sensor implanted in the exhaust gas flow is processed by an electronic system which then acts on the gasoline injection nozzles. The above-described assembly therefore enables the electrical signals to be conveyed between the sensor located inside the exhaust silencer and the various wires and electrical elements serving the central electronic system which controls the injection nozzles.

In greater detail, sensors are currently assembled with a platinum compound which is annealed at 900° C. The platinum provides, after the heat treatment, firstly a metallurgical link between the rear side of the sensor and the alumina strip which enables the sensor to be mechanically supported and, secondly, an electrical link between the heating resistor of the sensor on the rear surface of this sensor and the heating current leads supported by the rear side of the alumina strip. The signal output wiring of the pump (in a poor mixture sensor as described with reference to FIG. 5) and the ground is done by means of platinum wires with a diameter of approximately 50 μm, soldered by thermocompression firstly to the outputs of the sensor and, secondly, to the pads made for this purpose on the alumina strip. These two operations, assembly and wiring, are nevertheless lengthy and difficult and, in addition, entail a number of specific problems, namely:

differential expansion between the alumina support heated by the exhaust gases and the corundum substrate, heated to a temperature which is generally different by the resistor incorporated in its rear side. This entails repeated shearing of the metallurgical link between the rear side of the sensor and the alumina strip, which may lead to a break in the mechanical link between the sensor and its strip.

adsorption of water (always present in the exhaust gases) on the surface of the alumina strips for a temperature below 650° C., the effect of which is to make these strips conductive on the surface and, therefore, to short-circuit the deposited metallic tracks. This problem can be partially resolved by passivating the surface of the alumina strips and the metallizations by means of an impervious refractory enamel, but the absorption of water will occur, nonetheless, at the place where the passivation ends, namely at the place where the thermocompressed connection wires coming from the sensor are connected to the corresponding pads screen printed on the alumina strips.

miscellaneous, electrically conductive deposits due to the cracking of the additives used in the oil and fuels, additives which, despite the above-described passivation, also have the effect of short-circuiting the platinum connection at the place where they are thermocompressed on the corresponding pads screen printed on the alumina strips.

The invention provides a sensor which can overcome these problems.

SUMMARY OF THE INVENTION

The invention therefore concerns an electrochemical sensor with an integrated structure for the measurement of the relative concentration of reactive species contained in a fluid mixture comprising:

an elongated substrate comprising, lengthwise, a first detection zone, a second zone for the supporting and fixing of the sensor and a third electrical connection zone;

one or more electrochemical cells, at least one of which is sensitive to an excess level of one of the reactive species with respect to a defined stoichiometry, said cell being implanted directly in the first zone of he substrate;

electrical connection areas located in the third electrical connection zone;

conductive tracks of electrical connections deposited on the substrate and connecting the electrochemical cell or cells to the electrical connection areas located in the electrical connection zone;

an encapsulating layer of material impervious to said gaseous mixture covering at least the first and second zones, said layer encapsulating, in particular, the electrochemical cells and the connection tracks and having at least one aperture for the entry of gases towards the electrochemical cell;

a fixing part placed in the second fixing zone and preventing fluid from flowing from the first zone to the third zone.

BRIEF DESCRIPTION OF THE DRAWINGS

The various objects and features of the invention will appear more clearly from the following description, made by way of example with reference to the appended figures, of which.

DESCRIPTION OF PREFERRED EMBODIMENTS

Figure 7:
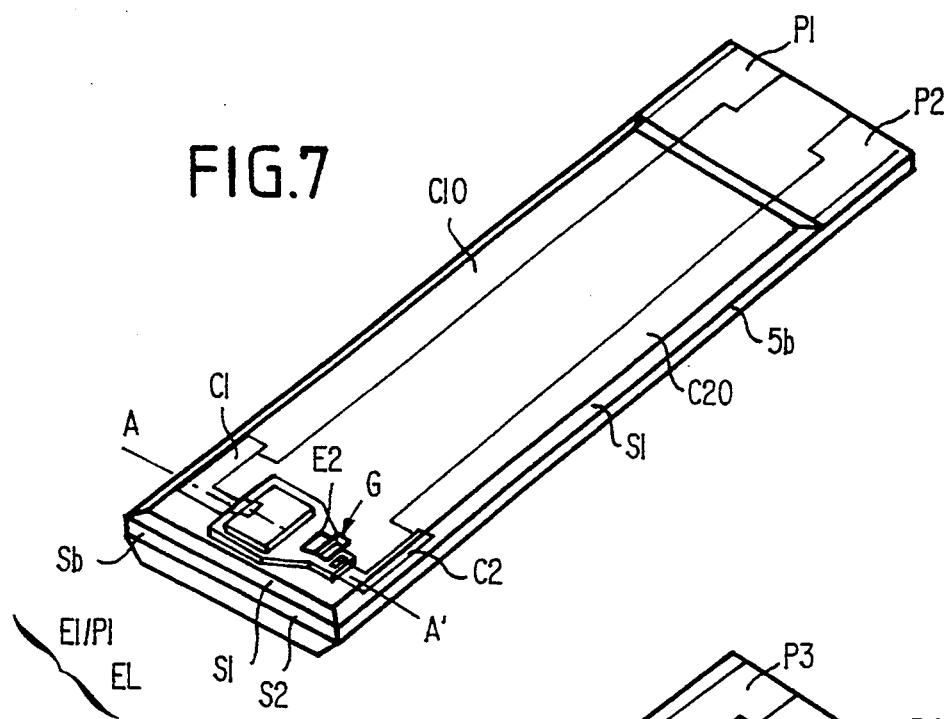
FIGS. 7 and 8 are views in perspective of an embodiment of a sensor according to the invention.
Figure 8:
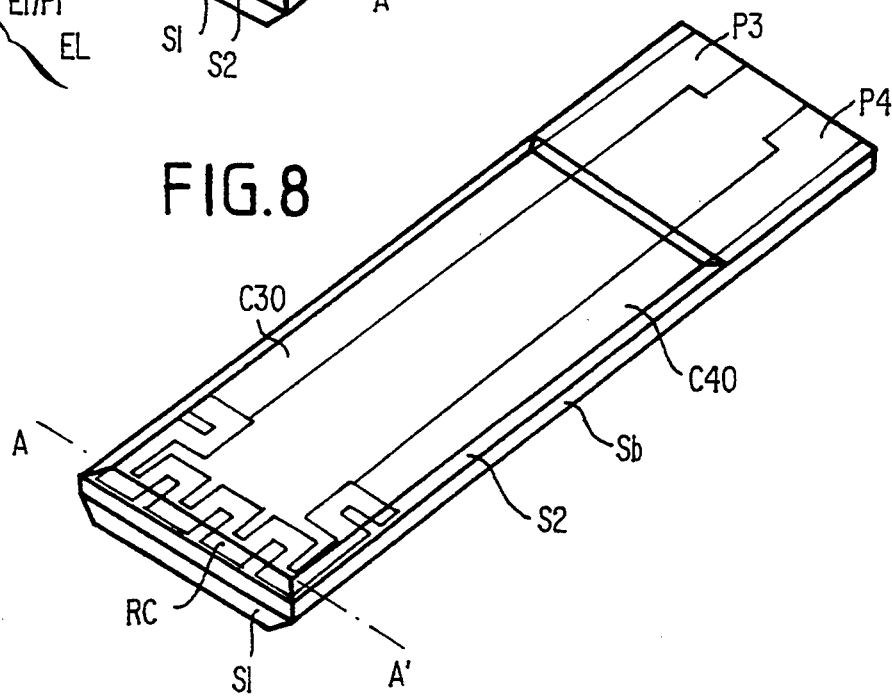
Figure 9:
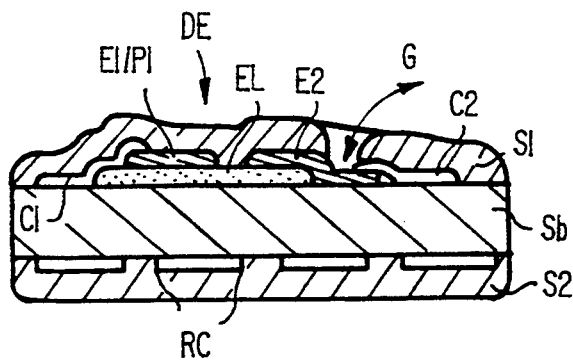
FIG. 9 is a sectional view of the sensor of FIGS. 7 and 8.

Referring to FIGS. 7 to 9, we shall first describe an embodiment of the sensor according to the invention.

This sensor has an elongated substrate plate Sb. At one end of the substrate, in a detection zone, there is made an electrochemical detection cell DE forming the active part of the sensor.

FIG. 9 shows a more detailed sectional view along AA' of this cell DE. By way of example, it has been shown similarly to the sensor of FIG. 3. It has:

the electrolyte EL made on the substrate Sb;

the electrodes E1/P1 and E2/P2, each covering a part of the electrolyte;

the electrical connectors C1, C2, connected to the electrodes E1/P1 and E2/P2;

the encapsulating layer S1, also called a sealing layer, possessing an inlet G enabling the inlet of the gas mixture to be analyzed.

In FIG. 7, it can be seen that the electrical connectors, C1 and C2, are extended by connection strips or conductors, C10 and C20, towards the end of the substrate opposite to the end supporting the cell DE. These conductors, C10 and C20, connect the connectors, C1 and C2, to connection areas, P1 and P2, located in a connection zone. The encapsulating layer S1 covers the detection zone and the intermediate zone located between the detection zone and the connection zone. This encapsulation layer S1 thus imperviously protects the cell DE, the connections C1, C2 and the conductors C10, C20. A gases inlet G is made in this encapsulating layer S1 to enable the passage of gases towards the cell DE and especially towards the electrolyte EL as shown in FIG. 9.

FIG. 8 shows a view in perspective showing that face of the sensor which is opposite to the one having the cell DE. This figure thus shows a heating resistor RC made on the substrate Sb facing the cell DE. This resistor can be seen in FIG. 9. The conductors C30 and C40 connect the ends of the resistor RC to connection areas P3 and P4 located in the connection zone of the substrate Sb. The detection zone of the substrate containing the resistor RC and the intermediate zone located between this detection and the connection zone are coated with an encapsulating layer S2 identical to S1.

In this way, as shown in FIGS. 7 and 8, the elongated sensor of the invention has, at one end, a cell DE located in a detection zone, connection areas located at the other end of the sensor and electrically connected to the cell DE, the entire unit being coated with one or more encapsulation layers, except for the gases inlet window G and the zone containing the connection areas which have to be electrically connected to other electronic or electromechanical elements.

The sensor according to the present invention is thus manufactured on a single substrate which is a good electrical insulator at high temperatures and which is chemically inert, namely a material such as, for example, alumina, corundum, beryllium oxide, aluminium nitride, a spinel group material, etc. The various active elements of the sensor (stabilized zirconium oxide, metal/metal oxide mixture, electrodes) are deposited in the form of layers at one end of a strip ($Al_2O_3$, BeO, $MgAl_2O_4$, AlN ...). These layers will all undergo appropriate firing cycles after deposition.

It is important to note that the first deposit of solid electrolyte (for example, stabilized zirconium oxide deposited by silk screen process) can be made on a substrate of untreated material (cast alumina for example). In this case, the electrolyte and substrate are fired and sintered simultaneously, for example at 1450°, for one to eight hours, and the following deposits will be fired normally, namely at 1400° C. for the electrodes, the Pd/PdO mixture and the heating resistor and 900° C. to 1200° C. for the enamel depending on its nature.

In another alternative embodiment, the substrate can be sintered simultaneously with the solid electrolyte and the two electrodes, namely the measuring and reference electrodes, as well as the Pd/PdO mixture at 1400° C. for one to eight hours. The enamel is then fired between 900° C. and 1200° C. depending on its composition.

The electrical inputs and outputs of the sensor will be routed from the electrodes by means of conducting tracks, generally metallic, deposited (if necessary by silk screen process) on the same substrate wafer. These tracks will be connected, by simple overlapping, to the electrodes in the active part of the sensor. The set comprising the active element and the conductor will be passivated by encapsulation with a refractory enamel (deposited by silk screen process for example) in which will be made only the aperture needed for the intake of gas samples for analysis. The heating resistor will be deposited (for example by silk screen process) on the rear face of the strip considered, so that the maximum temperature (above 650° C.) is located exactly beneath the aperture in the enamel (corresponding to the test sample intake region) thus preventing the various phenomena of adsorption and incorporation of water in front of the gas intake window G.

Figure 5:
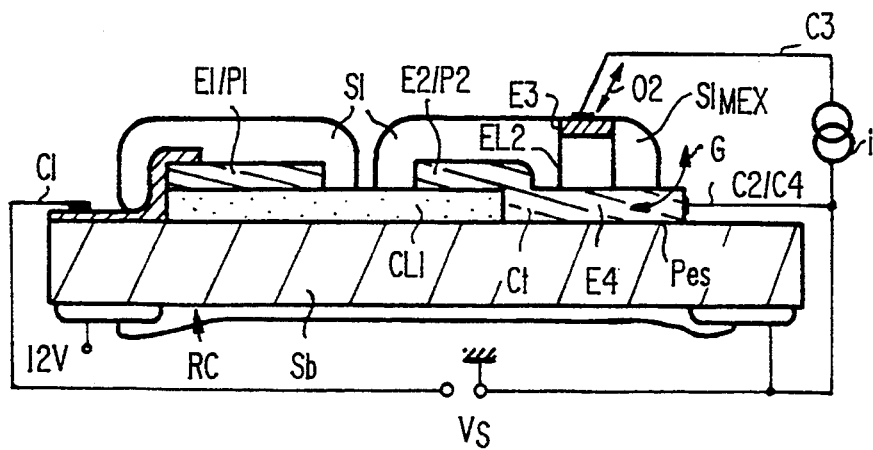
Figure 6:
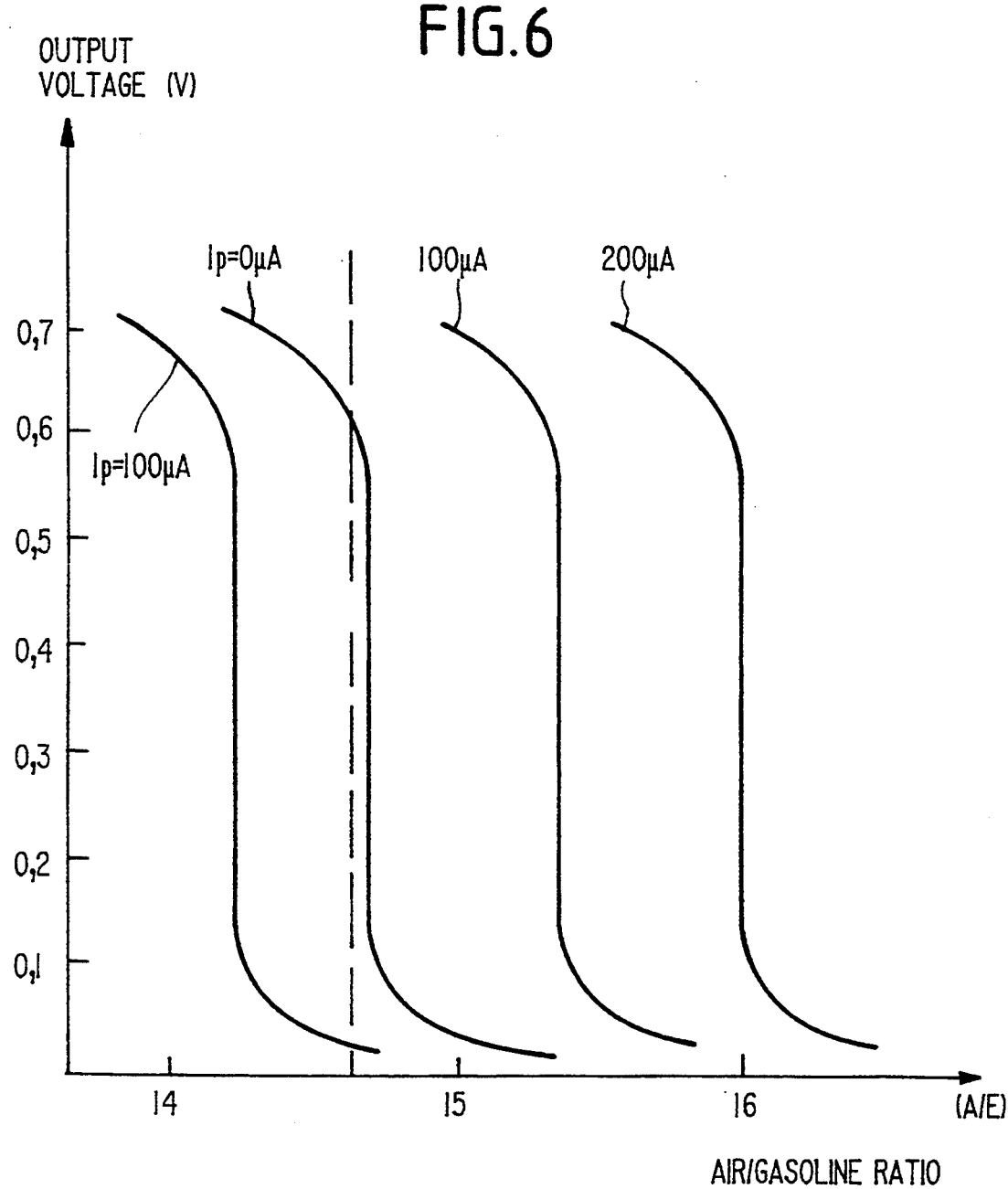
FIG. 6 shows response curves of a sensor according to FIG. 5.
Figure 10:
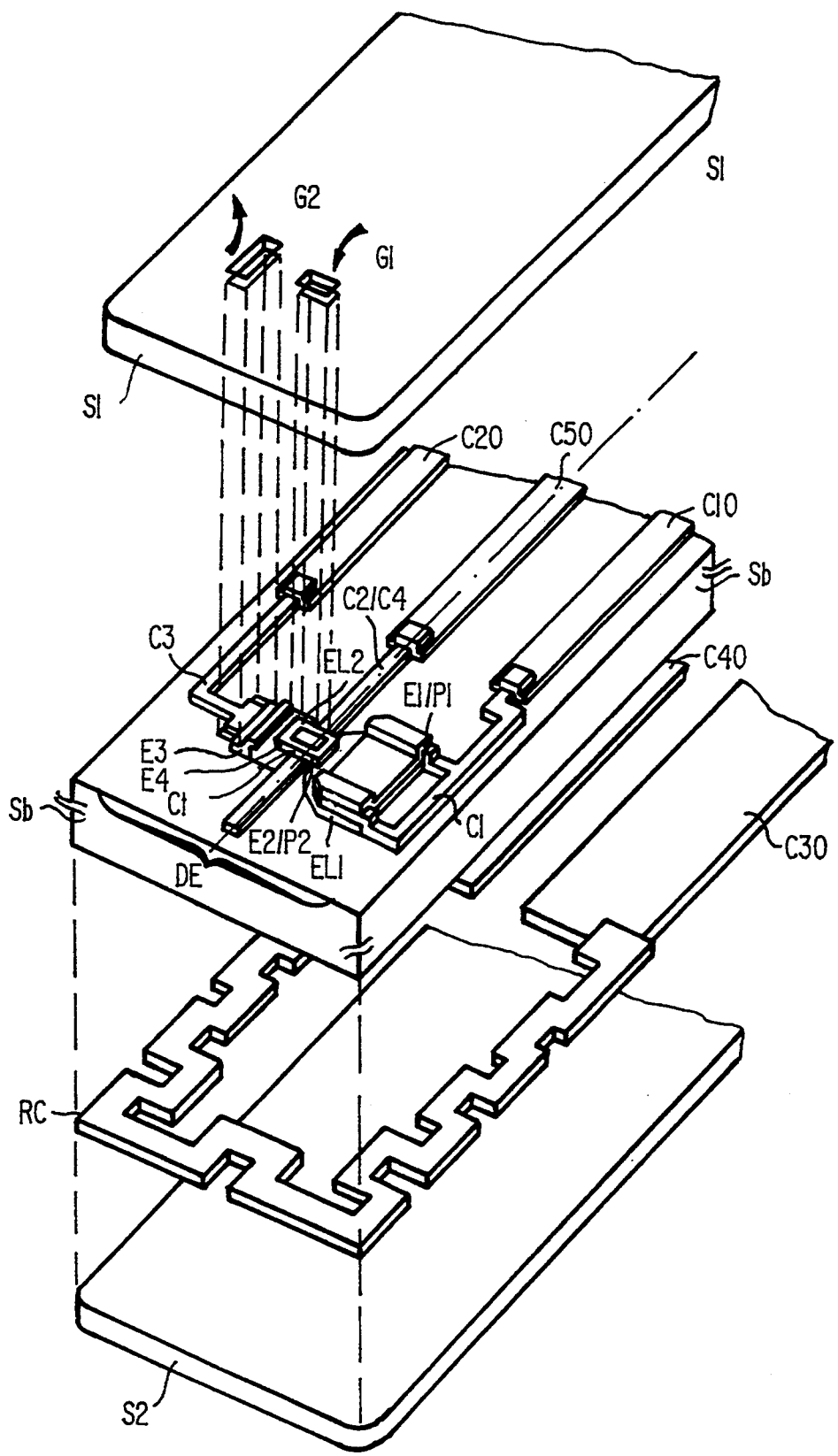
FIG. 10 is an exploded view of an example of a sensor according to the invention (the type of sensor of FIG. 5)

FIG. 10 shows a more detailed, exploded view of a sensor according to the invention in which the electrochemical cell DE is of a type similar to that of FIG. 5. As can be seen, the substrate Sb has, on one side, the electrochemical cell DE with the electrolytes E11, E12, a catalytic micro-chamber Ct, the electrodes E1/P1, E2/P2, E3 and E4 and connections C1, C2, C3 and 34. The entire unit is coated with a layer of enamel S1, having an inlet aperture G1 for gas to be analyzed and an aperture G2 used to pump out or remove oxygen. The other side of the substrate Sb has a resistor RC facing the electrochemical cell and connections C30, C40. An enamel layer S2 coats this side.

Figure 1:
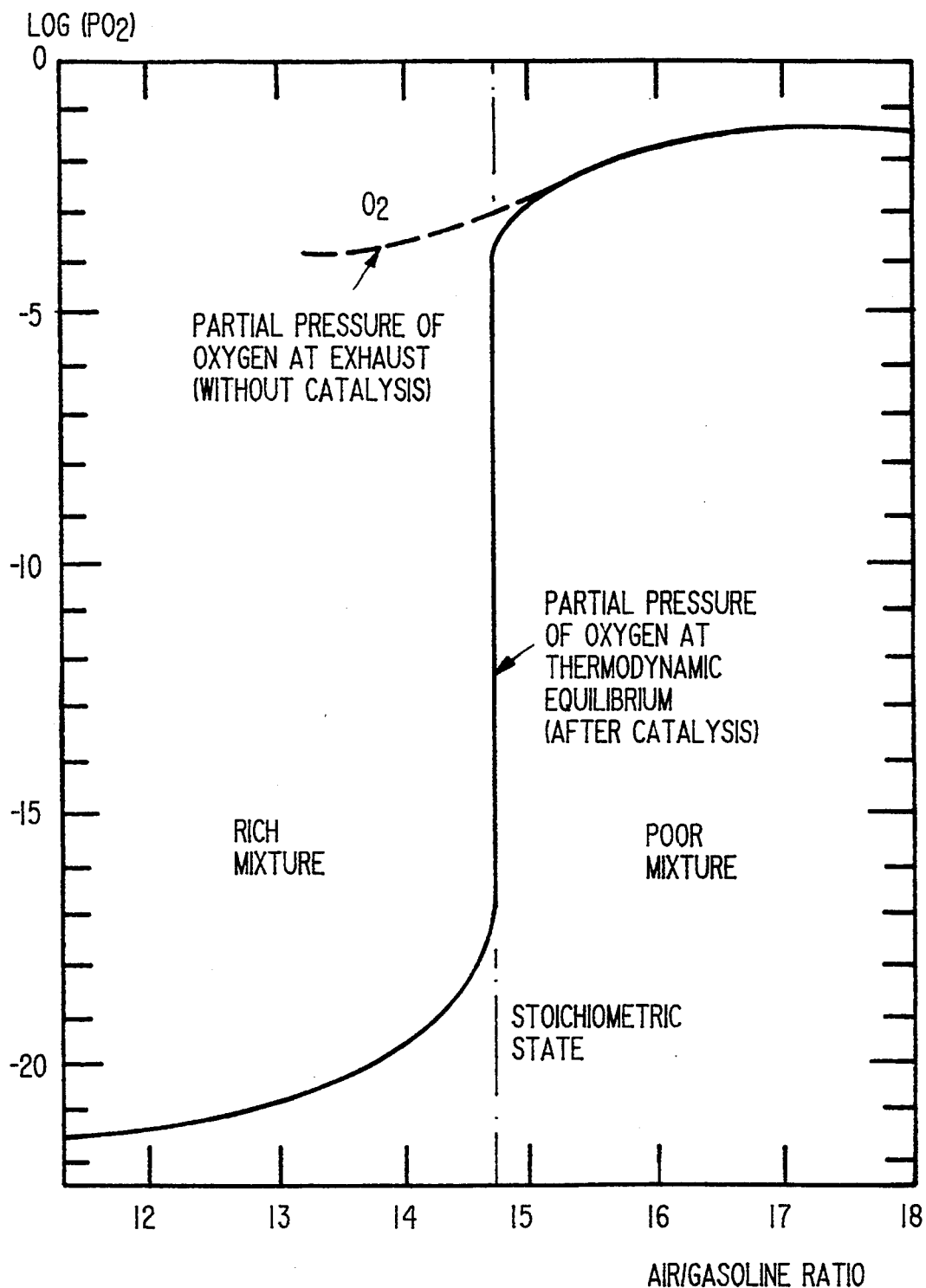
FIG. 1 is a graph showing the partial oxygen pressures in automobile exhaust gases.
Figure 2:
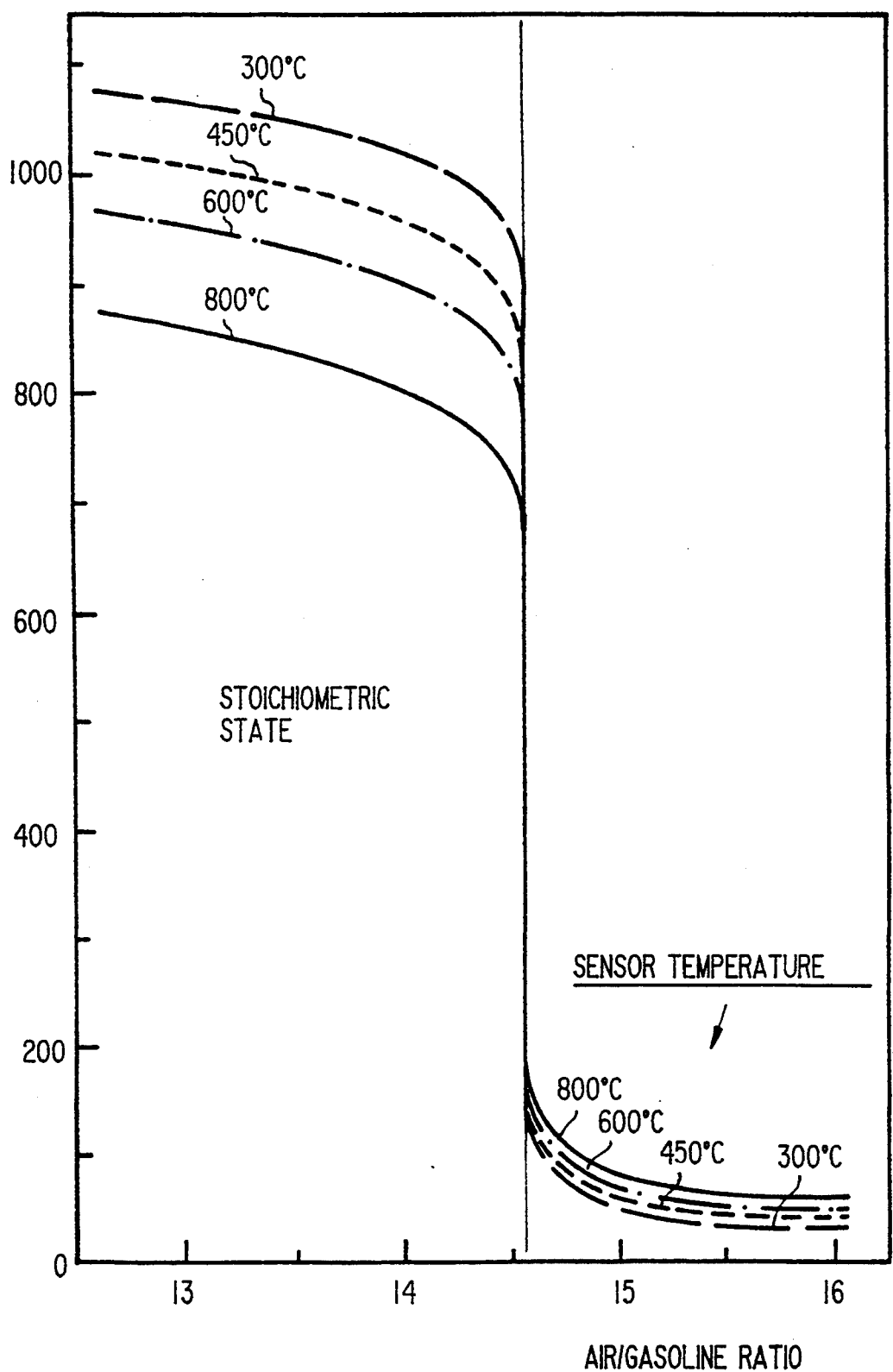
FIG. 2 shows voltage response curves of automobile sensors working with an air reference or a metal/oxidated metal reference.
Figure 3:
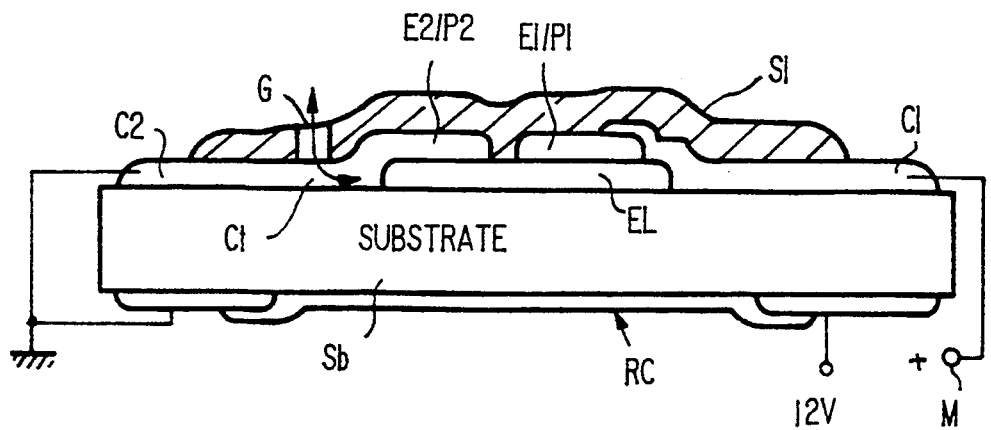
FIGS. 3 to 5 show embodiments of prior art sensors already described above.
Figure 4:
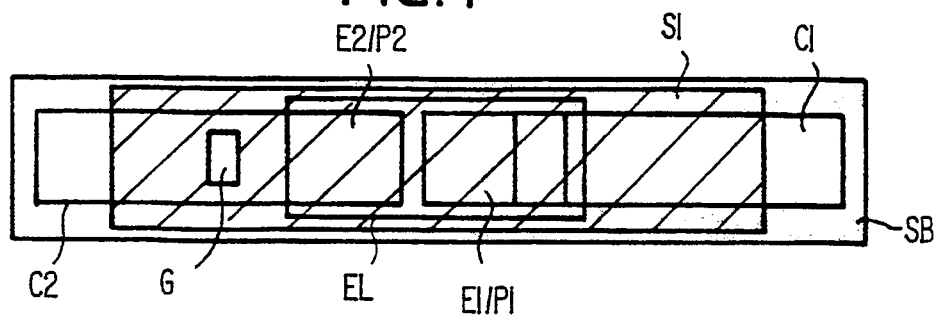

Referring to the schematic diagrams of FIGS. 3 and 5, it is seen that, owing to the use of an internal solid reference of the metal/metal oxide type, the electric insulating impedance between the measuring electrode and the reference electrode must be high. For, any electric transfer between these two electrodes results in a concomitant transfer of oxygen from the electrode where the partial pressure is at its highest to the electrode where this pressure is at its lowest.

Assuming a temperature of about 800° C., the oxygen pressure above the reference, for example a pressure imposed by the Pd/PdO (0,2 Atm) mixture, is always higher than the pressure prevailing in the exhaust silencer (less than 0.1 Atm). Thus, any electric short circuit between the measuring and the reference electrodes may result, at the end of a period depending on the amplitude of the short circuit, in the complete reduction of the oxide PdO included in the Pd/PdO mixture. The potential assumed by the reference electrode then becomes random, and this electrode no longer plays its reference role, thus making the entire sensor inoperative.

To avoid this drawback, the insulating support (which is the main cause of short circuits between the measuring and reference electrodes) must have very high resistivity at high temperatures, so as to insulate both electrodes.

Thus, to ensure a lifetime of about 2000 hours, given the geometrical configurations of the sensors, the resistivity, at 800° C., of the insulating support should be about $10^8$ ohms cm and, in all cases, it should be greater than $10^7$ ohms cm.

Thus, this type of a structure of the sensor can be designed only by using, in particular, a highly pure material of the $Al_2O_3$ type (with an $Al_2O_3$ content ranging between 99.3% and 99.9%) with an optimized grain size. For example, the resistivity, at 800° C., of a sapphire substrate is of the order of some $10^{12}$ ohms cm.

Figure 11:
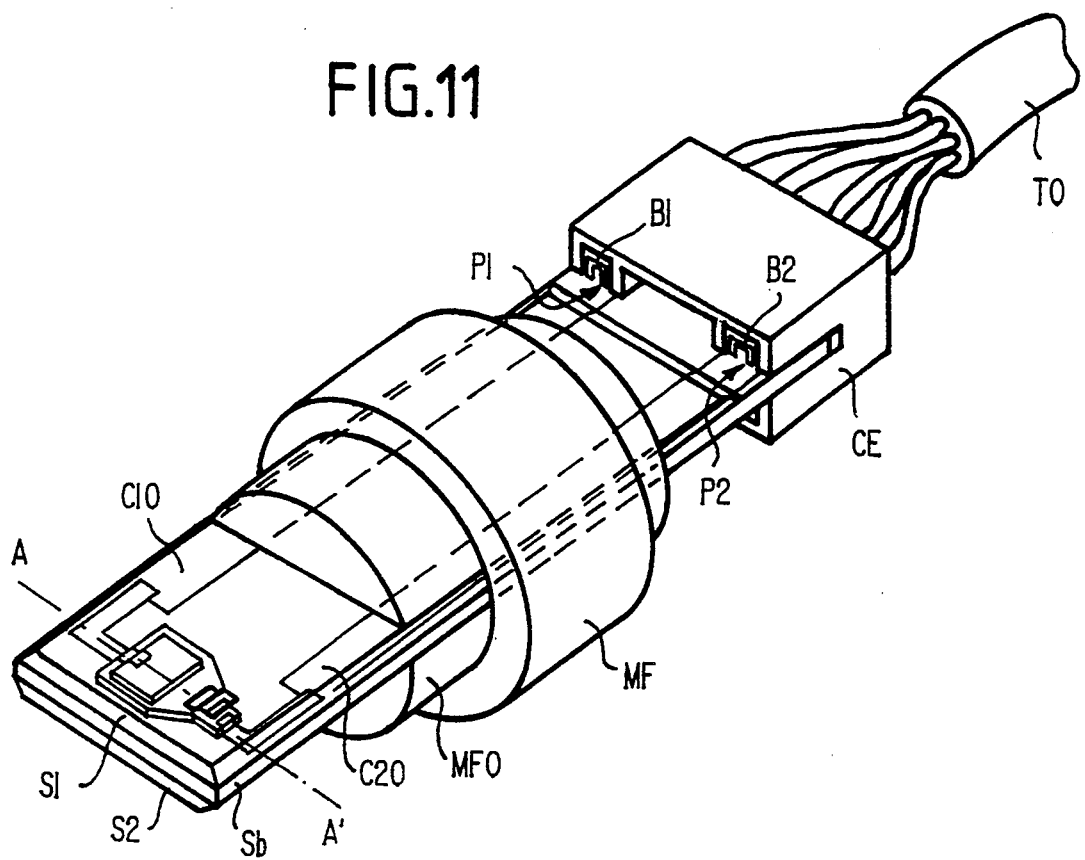
FIG. 11 is a view in perspective of the sensor of FIGS. 7 and 8 comprising fixing means and electrical connection means.

Referring to FIG. 11, we shall now describe a more complete embodiment of the sensor according to the invention. This figure again shows the sensor of FIGS. 7 to 9.

In the intermediate part, called a fixing zone, located between the detection zone and the connection zone, there is a fixing part MF. This fixing part is fastened rigidly and imperviously to the encapsulation layers S1, S2 of the sensor. The part MF may have a constricted part MFO, which may be threaded if necessary, enabling the sensor to be mounted in the wall of a housing.

Figure 12:
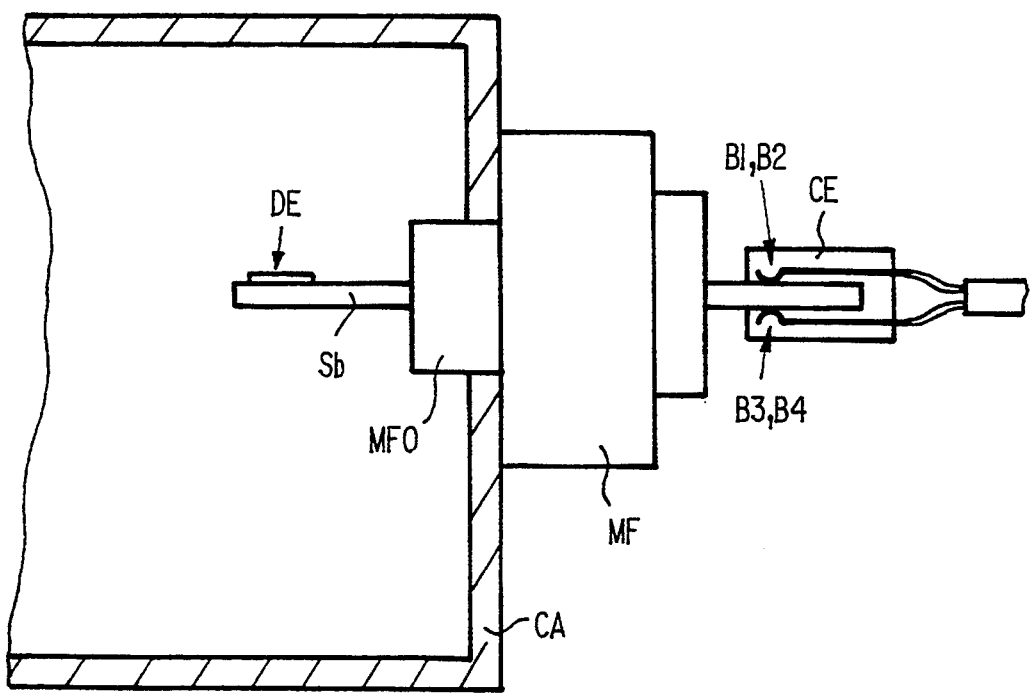
FIG. 12 is an example of assembly of the sensor of FIG. 10.

Thus, as shown in FIG. 12, the part MFO of the fixing part MF is mounted in a housing CA, the cell DE made at the left-hand end of the sensor is located inside the housing CA in which there is the gaseous mixture to be analyzed or regulated. The connector CE is thus isolated from the gas mixture by the fixing part MF and the housing CA.

As shown in FIGS. 11 and 12, the substrate Sb is plugged into a connector CE in the connection zone. Connecting elements (B1, B2, B3, B4 for example) are connected to the connection areas (P1, P2, P3, P4) and enable the connection of the electrical circuits of the sensor to a cable TO towards external circuits which are beyond the scope of the invention.

Figure 13:
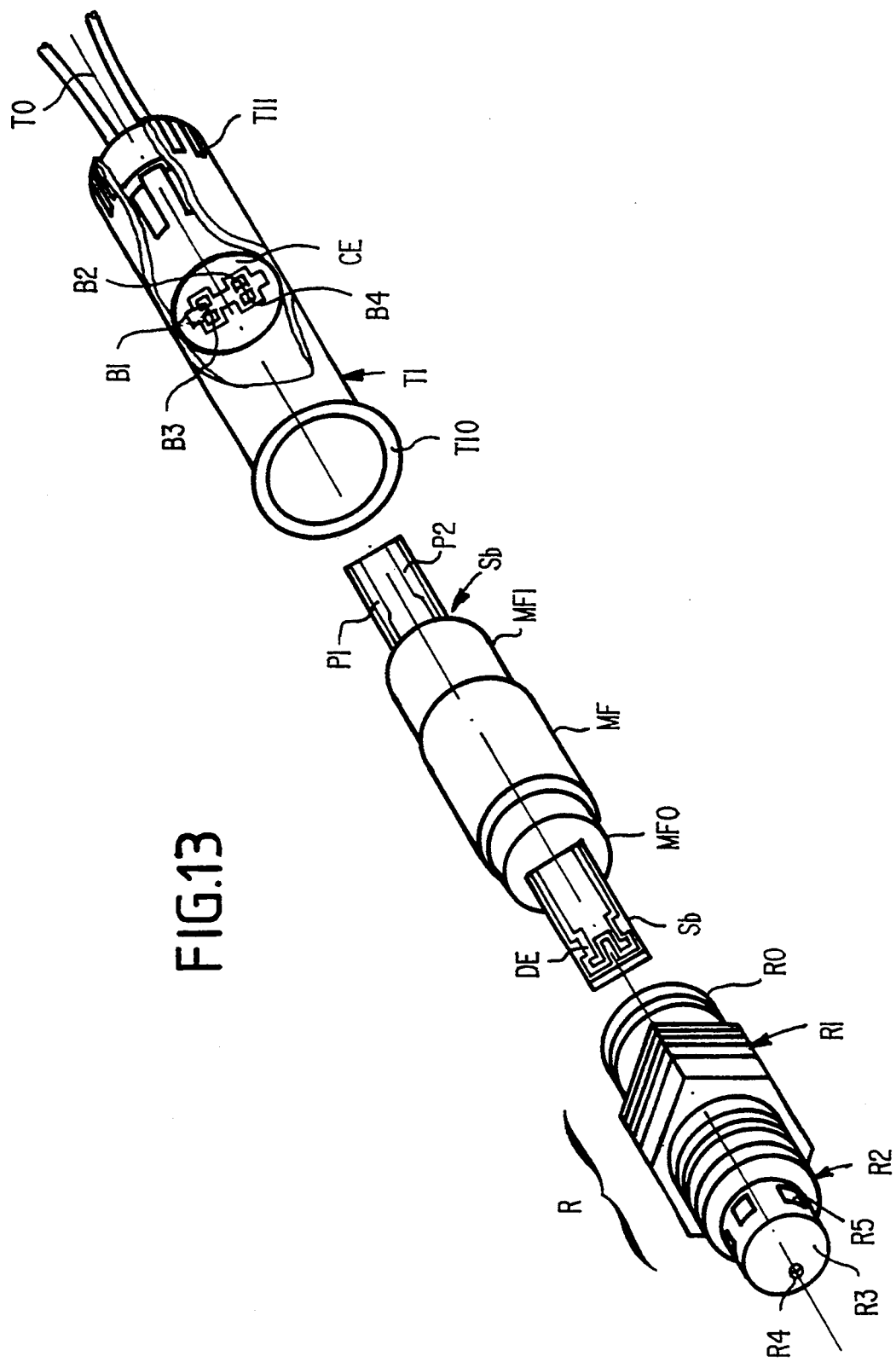
FIG. 13 is an exploded view of an exemplary embodiment of the sensor according to the invention.
Figure 14:
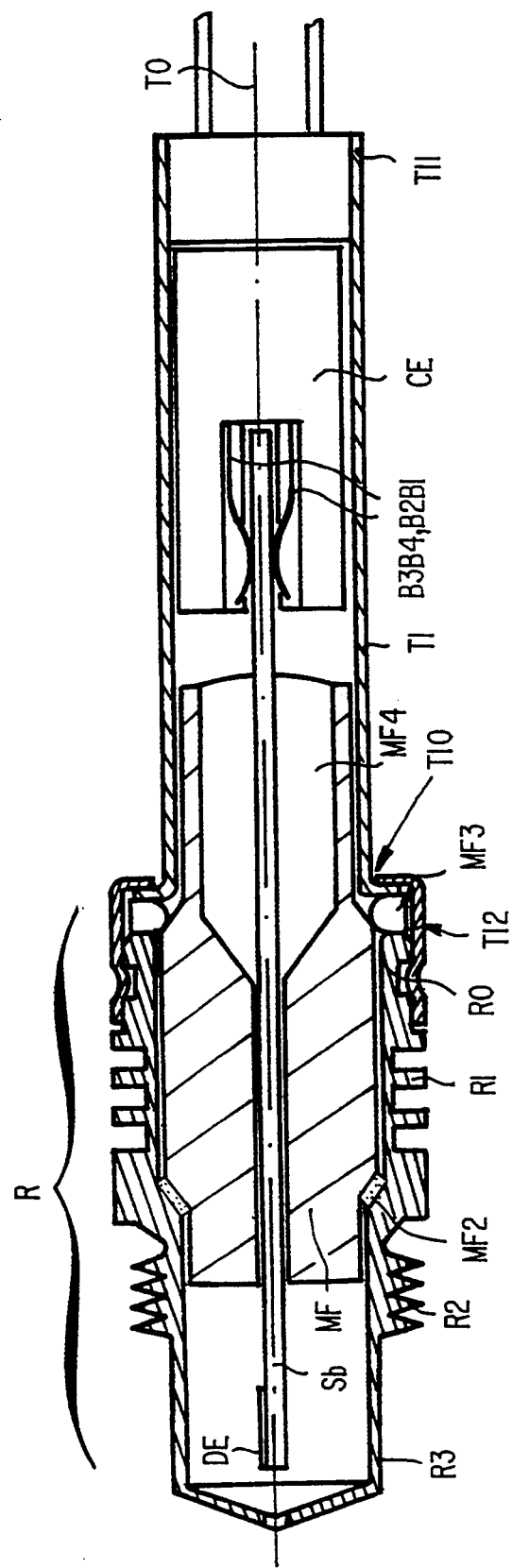
FIG. 14 is a sectional view of an exemplary embodiment of the sensor according to the invention.

Referring to FIGS. 13 and 14, we shall now give a detailed description of an embodiment of a sensor according to the invention.

FIG. 13 again shows:

the substrate wafer Sb bearing, in particular, the electrochemical cell DE and the connection areas P1, P2;

the fixing part MF, comprising fixing parts MF0 and MF1;

the connector CE with the connecting pins B1, B2, B3, B4, and the cable TO.

The sensor additionally has a metallic mounting part R to mount the sensor in a housing (not shown). This mounting part is used to mount the sensor in a housing instead of directly mounting the part MF as shown in FIG. 12.

The mounting part R is hollow so that it can take the wafer Sb and the cell DE. It has:

a part RO which fits onto the part MF0 of the fixing part MF;

cooling vanes R1;

a threaded part R2 used to mount the part R in a threaded part of the housing;

a shielding cap R3 that shields the electrochemical cell DE located inside. This shielding cap R3 has apertures R4, R5, for the flow of the gas to be analyzed.

Furthermore, a package T1 is fitted, by an end T10, on to the part MF1 of the fixing part MF. The connector CE is mounted on and fixed to the other end T11, and inside the housing T1, in such a way that the pins B1, B2, B3, B4 are connected to the connection areas such as P1, P2, P3, P4, of the sensor.

The unit thus described is mounted as shown in a sectional view in FIG. 14. Furthermore, the assembly is made impervious so that the exhaust gases do not reach the connection zone of the sensor. To this end, the wafer of the sensor is sealed into the fixing part NF by means of a refractory cement MF4. Gaskets MF2, MF3, provide imperviousness between the fixing part MF and the mounting part R on the one hand and the mounting part R and the package T1 on the other hand.

The package T1 is crimped, in its part T10, by a ring T12, on to the mounting part R and, in its part T11, to the connector CE.

Figure 15:
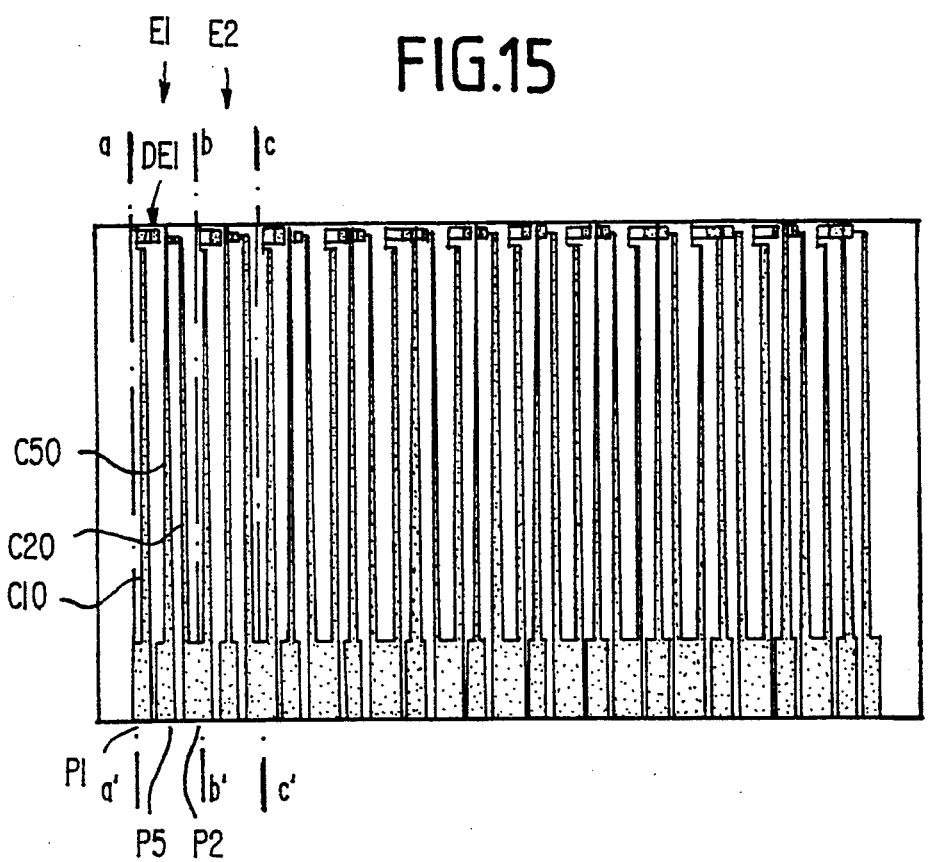
FIGS. 15 and 16 show an example of the making of several electrochemical cells according to the invention, jointly on one and the same plate.
Figure 16:
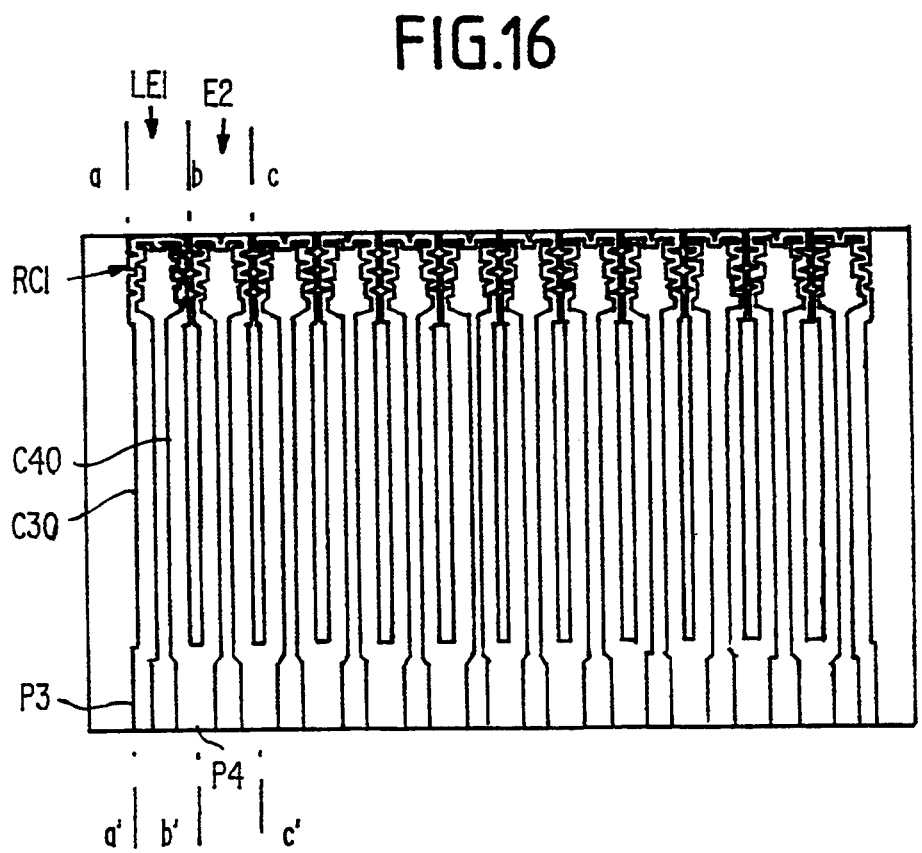

FIGS. 15 and 16 illustrate a method for making the strips, carrying electrochemical cells, jointly.

On one and the same wafer substrate several electrochemical cells are made side by side, with the connections C10, C20, C50 and the connection areas P1, P2, P5. As shown in FIG. 15, several cells such as DE1 are thus obtained. These cells are evenly spaced out. It must be noted that the sensors shown in FIG. 15 are of the type described with reference to FIGS. 5 and 10: this explains the existence of a connection area P5 and of the connection conductor C50 connecting this area to the cell DE.

FIG. 16 shows the opposite face of the wafer carrying the electrochemical cells. This face has resistors such as RC1, located in zones each corresponding to an electrochemical cell as well as the connections C30, C40, and the connection regions P3, P4.

The wafer is cut out along the lines shown by the dots and dashes aa', bb', cc' so as to obtain a sensor carrying, on one face, an electrochemical cell and the corresponding connections and, on the other face, a resistor RC and the corresponding connections.

The sensors obtained are all identical.

For example, the materials used to make a sensor of this type may be:

for the electrolyte: an yttria zirconium oxide material;

for the electrodes: a cermet (ceramic/metal alloy material);

for the connections and conducting elements: metallic layers;

for the encapsulating layers and the material providing imperviousness between the fixing part MF and the wafer of the sensor: a refractory sealing enamel.

As described above, the method for making the wafer of the sensor could provide for depositing the electrolyte EL of the cell on the substrate wafer Sb and then for sintering all these elements simultaneously. The electrodes are then deposited and, after this, they are annealed. Finally, the electrical circuits (electrical conductors and connection areas) and the enamel layer are made and all the elements are again sintered simultaneously between 900° C. and 1200° C., depending on the nature of the materials.

The method of the invention also provides for making of the the electrolyte and the electrodes on the untreated substrate wafer. All these elements are then sintered simultaneously. The electrical circuits are made and then the enamel layer is deposited and then annealed and the unit is made to undergo firing treatment.

For making several sensors jointly on one and the same plate, according to the method of the invention, after the annealing of the enamel, the plate is cut out to obtain the different individual sensors in the form of strips.

The fixing and supporting part MF should be made of a material with an expansion coefficient matching that of the substrate Sb material. For example, if the substrate is alumina, the part MF will preferably be made of alumina also. Similarly, the sealing cement MF4 will be made of a material with an expansion coefficient matching that of the materials of the part MF or the substrate Sb.

It is quite clear that the above description has been made only as a non-restrictive example and that other alternatives can be considered without going beyond the scope of the invention. The numerical examples and the choices of materials, in particular, have been given only to illustrate the description.

What is claimed is:

1. An electrochemical sensor with an integrated structure for the measuring of the relative concentration of a reactive species contained in a fluid mixture comprising:

an elongated insulating chemically inert substrate made of alumina having a $Al_2O_3$ content ranging between 99.3 and 99.9%, said substrate having a shape of a flat and elongated plate, comprising, located on a same face of the plate, lengthwise, a first detection zone located at a first end of the plate, a second zone located at substantially the middle of the plate for the supporting and fixing of the sensor and a third electrical connection zone located at a second end opposite to the first end;

at least one electrochemical cell having a solid zirconium oxide electrolyte, at least one of which is sensitive to an excess level of one of the reactive species with respect to a defined stoichiometry, said cell being implanted in the first zone of the substrate;

electrical connection areas located in the third electrical connection zone;

conductive tracks deposited on the substrate and connecting the electrochemical cell or cells to the electrical connection areas located in the electrical connection zone;

an encapsulating layer of material impervious to said gaseous mixture covering at least the first and second zones, said layer encapsulating, in particular, the electrochemical cells and the conductive tracks and having at least one aperture for the inlet of gases towards the electrochemical cells;

a fixing part placed in the second zone and preventing fluid from flowing between the first zone and the third zone, wherein said fixing part has mounting means used to fix the sensor to a wall of a housing in such a way that the electrochemical cell is located within the housing containing the gaseous mixture to be analyzed and that the wall of the housing associated with the fixing part prevents the gases from flowing towards the said electrical connection zone.

2. A sensor according to claim 1, wherein the electrochemical cell comprises a layer of said solid electrolyte, made on the substrate and in contact with a plurality of electrically conductive electrodes, one of said electrodes being placed in contact with the gas inlet aperture whereby diffusion of said reactive species is accomplished.

3. A sensor according to claim 1, further comprising a female connector mounted on the third electrical connection zone and having connection pins put into contact with said connection areas.

4. A sensor according to claim 1, wherein the substrate and the fixing part are made of materials with matching expansion coefficients.

5. A sensor according to claim 4, wherein the fixing part is made of alumina.

6. A sensor according to claim 1, wherein said mounting means comprises a threaded part and cooling vanes.

7. An electrochemical sensor according to claim 1, wherein said at least one electrochemical cell, sensitive to an excess of one of the reactive species, is implanted on one face of the substrate.

* * * * *